United States Patent
Nishida et al.

(10) Patent No.: US 9,201,033 B2
(45) Date of Patent: Dec. 1, 2015

(54) WATER-CONCENTRATION DETECTION DEVICE

(75) Inventors: Chieko Nishida, Tokyo (JP); Tatsuya Yabe, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 13/983,074

(22) PCT Filed: Apr. 2, 2012

(86) PCT No.: PCT/JP2012/058973
§ 371 (c)(1),
(2), (4) Date: Aug. 1, 2013

(87) PCT Pub. No.: WO2012/157349
PCT Pub. Date: Nov. 22, 2012

(65) Prior Publication Data
US 2013/0313111 A1    Nov. 28, 2013

(30) Foreign Application Priority Data
May 18, 2011   (JP) .................. 2011-111419

(51) Int. Cl.
*G01N 27/02*   (2006.01)
*G01N 27/07*   (2006.01)
(Continued)

(52) U.S. Cl.
CPC .............. *G01N 27/02* (2013.01); *G01N 27/048* (2013.01); *G01N 27/06* (2013.01)

(58) Field of Classification Search
CPC ...... G01N 27/02; G01N 27/048; G01N 27/06
USPC .......... 73/23.2, 29.01, 29.02, 335.01–335.14; 422/50, 420–429, 68.1, 82.01–82.04, 422/83, 88, 98
See application file for complete search history.

(56) References Cited

U.S. PATENT DOCUMENTS

2005/0081625 A1* 4/2005 Chen et al. .................. 73/335.02
2005/0233463 A1   10/2005 Dominelli et al.

FOREIGN PATENT DOCUMENTS

CN    201184872 Y    1/2009
JP    2-297050 A    12/1990
(Continued)

OTHER PUBLICATIONS

Su, Pi-Guey, I. Cherng Chen, and Ren-Jang Wu. "Use of poly (2-acrylamido-2-methylpropane sulfonate) modified with tetraethyl orthosilicate as sensing material for measurement of humidity." Analytica chimica acta 449.1 (2001): 103-109.*

(Continued)

*Primary Examiner* — Lyle Alexander
*Assistant Examiner* — Robert Eom
(74) *Attorney, Agent, or Firm* — Buchanan Ingersoll & Rooney PC

(57) ABSTRACT

A water-concentration detection device is configured to detect a water concentration of insulating gas filled in a gas-insulated device. The water-concentration detection device includes: a gas chamber in which the insulating gas introduced from the gas-insulated device is enclosed; electrodes that are porous and are arranged to face each other within the gas chamber; a solid electrolyte membrane that is hydrogen-ion conductive and is held between and fixedly attached to the electrodes; an impedance measurement unit that measures an alternating-current impedance between the electrodes by applying an alternating-current voltage to the electrodes; a water-concentration detection unit that detects the water concentration of the insulating gas based on the alternating-current impedance measured by the impedance measurement unit; and a drying unit that removes water from an atmosphere in the gas chamber before the insulating gas is introduced into the gas chamber from the gas-insulated device.

7 Claims, 5 Drawing Sheets

(51) Int. Cl.
*G01N 27/04* (2006.01)
*G01N 27/06* (2006.01)

(56) References Cited

FOREIGN PATENT DOCUMENTS

| JP | 3-40553 U | 4/1991 |
|---|---|---|
| JP | 4-49856 U | 4/1992 |
| JP | 5-49285 A | 2/1993 |
| JP | 5-144645 A | 6/1993 |
| JP | 5-49285 B2 | 7/1993 |
| JP | 2000-275199 A | 10/2000 |
| JP | 2003-75385 A | 3/2003 |
| JP | 2005-300549 A | 10/2005 |
| JP | 2006-308502 A | 11/2006 |

OTHER PUBLICATIONS

Fürjes, P., et al. "Porous silicon-based humidity sensor with interdigital electrodes and internal heaters." Sensors and Actuators B: Chemical 95.1 (2003): 140-144.*

International Search Report (PCT/ISA/210) issued on Jun. 26, 2012, by the Japanese Patent Office as the International Searching Authority for International Application No. PCT/JP2012/058973.
Written Opinion (PCT/ISA/237) issued on Jun. 26, 2012, by the Japanese Patent Office as the International Searching Authority for International Application No. PCT/JP2012/058973.
Eiichi Nagao et al., Moisture Detection of $SF_6$ Gas Instruments by Solid Electrolyte, Heisei 17 Nen National Convention Record I.E.E. Japan, 2005, pp. 244-245.
Eiichi Nagao et al., Moisture Detection of $SF_6$ Gas Instruments by Solid Electrolyte, Helsel 17 Nen Proceedings of the Annual Conference of Power & Energy Society, 2005, pp. 40-1-40-2.
Mitsuhito Kamei et al., Study of Water Detecting Sensor in Insluated Gas of GIS/GCB Electrochemical Sensor Using Ttriethlenediaminesulfate as Electrolyte, The Transactions of the Institute of Electrical Engineers of Japan E, Nov. 2, 2010, vol. 130, No. 11, pp. 531-536.
Notification of the First Office Action issued on Aug. 5, 2014, by the State Intellectual Property Office of The People's Republic of China in Chinese Patent Application No. 201280014340.9, and an English translation of the Office Action (12 pages).

* cited by examiner

WATER-CONCENTRATION DETECTION DEVICE

FIELD

The present invention relates to a water-concentration detection device that detects a concentration of water in insulating gas filled in a gas-insulated device.

BACKGROUND

A gas-insulated device is filled with insulating gas such as $SF_6$ gas. In a conventional water-concentration detection device present in $SF_6$ gas, a water sensor that detects water is installed in a gas-insulated device. This water sensor is configured to include porous electrodes provided to face each other and a hydrogen-ion conductive solid electrolyte membrane that is provided between the porous electrodes and in equilibrium with the water concentration of $SF_6$ gas. This water-concentration detection device measures a water concentration of $SF_6$ gas by applying an alternating-current (AC) voltage to the porous electrodes and measuring inter-electrode AC impedance changing correspondingly to the water concentration of the $SF_6$ gas (see Patent Literature 1).

CITATION LIST

Patent Literature

Patent Literature 1: Japanese Patent Application Laid-open No. 2006-308502

SUMMARY

Technical Problem

The water concentration of insulating gas in an actually used gas-insulated device normally ranges several tens of ppm to several hundreds of ppm. Therefore, the water sensor of the water-concentration detection device described above is arranged in the above described environment. In this case, when the water concentration decreases to as low as several hundreds of ppm or several tens of ppm, the AC impedance of the solid electrolyte membrane increases exponentially from about 10 ohms to become equal to or higher than 1 megaohm to follow the decrease in the water concentration (see Patent Literature 1).

Meanwhile, in the atmospheric environment, the water concentration is several tens of thousands of ppm (10000 ppm) or more and largely differs from the water concentration within the gas-insulated device. Accordingly, if the solid electrolyte membrane of the water sensor in equilibrium with, for example, the water concentration of the atmospheric environment before a measurement is arranged in the gas-insulated device, it takes a considerably long time until this solid electrolyte membrane reaches a state of equilibrium with the water concentration of several tens of ppm to several hundreds of ppm in the gas-insulated device, and it takes a few hours to a few days or more until the water sensor indicates a certain measured value. Therefore, there is a problem that it is impossible to obtain a measurement result in a short period of time.

The present invention has been achieved to solve the above problems, and an object of the present invention is to provide a water-concentration detection device capable of detecting a water concentration in a short period of time.

Solution to Problem

According to an aspect of the present invention a water-concentration detection device for detecting a water concentration of insulating gas filled in a gas-insulated device, the water-concentration detection device includes: a gas chamber in which the insulating gas introduced from the gas-insulated device is enclosed; electrodes that are porous and are arranged to face each other within the gas chamber; a solid electrolyte membrane that is hydrogen-ion conductive and is held between and fixedly attached to the electrodes; an impedance measurement unit that measures an alternating-current impedance between the electrodes by applying an alternating-current voltage to the electrodes; a water-concentration detection unit that detects the water concentration of the insulating gas based on the alternating-current impedance measured by the impedance measurement unit; and a drying unit that removes water from an atmosphere in the gas chamber before the insulating gas is introduced into the gas chamber from the gas-insulated device, before start of measuring the water concentration.

Advantageous Effects of Invention

According to the present invention, a water concentration can be detected in a short period of time.

DESCRIPTION OF EMBODIMENTS

Exemplary embodiments of a water-concentration detection device according to the present invention will be explained below in detail with reference to the accompanying drawings. The present invention is not limited to the embodiments.

First Embodiment

Figure 1:
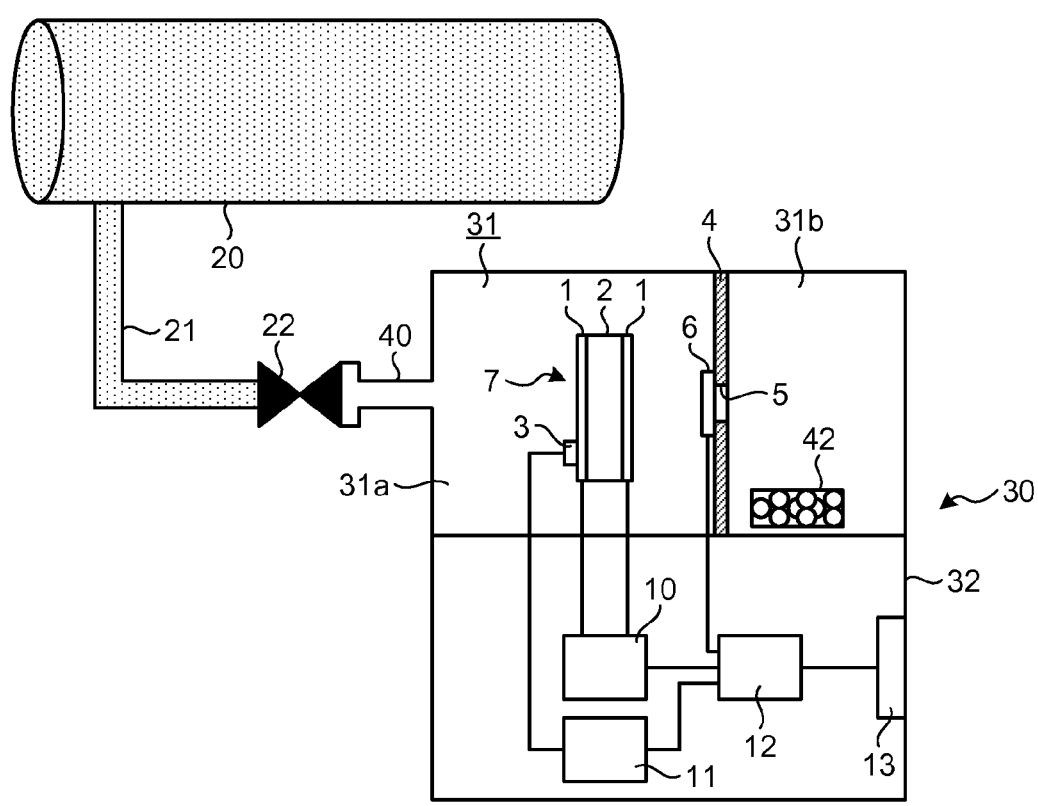
FIG. 1 is a configuration diagram of a water-concentration detection device according to a first embodiment.

FIG. 1 is a configuration diagram of a water-concentration detection device according to a first embodiment of the present invention. FIG. 1 depicts a gas-insulated device 20 filled with insulating gas, for example, $SF_6$ gas and a water-concentration detection device 30 attached to the gas-insulated device 20. Specifically, the water-concentration detection device 30 is connected to the gas-insulated device 20 by attaching an attachment port 40 of the water-concentration detection device 30 to a pipe 21 of the gas-insulated device 20 via a valve 22. When the valve 22 is opened, the insulating gas within the gas-insulated device 20 is introduced into the water-concentration detection device 30 via the pipe 21 and the insulating gas is used as sampling gas.

For example, the water-concentration detection device 30 is a portable water-concentration detection device and includes a gas chamber 31 and a signal processing unit 32. The gas chamber 31 includes a gas chamber 31a (first gas chamber) and a gas chamber 31b (second gas chamber) which are partitioned by a wall 4. A communication path 5 that communicates the gas chambers 31a and 31b with each other and a valve 6 capable of opening or closing the communication path 5 are provided on the wall 4.

The gas chamber 31a is a chamber that is directly connected to the gas-insulated device 20 via the pipe 21 and the valve 22, and the insulating gas introduced from the gas-insulated device 20 can be enclosed in the gas chamber 31a as the sampling gas by opening the valve 22. A pair of porous electrodes 1 arranged to face each other and a solid electrolyte membrane 2 held between the electrodes 1 and fixedly attached to the electrodes 1 are arranged in the gas chamber 31a.

The electrodes 1 are formed by, for example, performing an electroless plating of platinum and the electrodes 1 are microscopically porous. By using the electrodes 1, it is possible to facilitate permeating water contained in the insulating gas into the solid electrolyte membrane 2. The solid electrolyte membrane 2 is constituted by, for example, hydrogen-ion conductive polymer and a water content of the solid electrolyte membrane 2 is in equilibrium with a water concentration of the insulating gas. That is, the water content increases proportionally with an increase in the water concentration of the insulating gas, and conversely decreases proportionally with a decrease in the water concentration thereof. For example, NAFION® manufactured by Du Pont can be used as the solid electrolyte membrane 2. As described later, the electrodes 1 and the solid electrolyte membrane 2 constitute an impedance element 7 that serves as a water sensor.

For example, a temperature sensor 3 is attached to one of the electrodes 1. The temperature sensor 3 is configured to include a resistance temperature sensor such as a Pt100 (a platinum resistor). Because being attached to the electrodes 1, the temperature sensor 3 can measure a gas temperature in the vicinity of the solid electrolyte membrane 2.

An absorbent 42 is arranged in the gas chamber 31b. The absorbent 42 absorbs water within the gas chamber 31 and can render an atmosphere in the vicinity of the solid electrolyte membrane 2 an extremely dry state. Preferably, a highly absorptive absorbent is used as the absorbent 42.

An impedance measurement circuit 10, a temperature measurement circuit 11, a computation unit 12, a display unit 13 are provided in the signal processing unit 32.

The impedance measurement circuit 10 is connected to the electrodes 1 and measures an alternating-current (AC) impedance between the electrodes 1 (that is, an AC impedance of the solid electrolyte membrane 2) by applying an AC voltage to the electrodes 1 (an impedance measurement unit). The impedance measurement circuit 10 is configured to include, for example, an AC power supply (not shown) applying the voltage to the electrodes 1 and a voltage divider-resistor (not shown) detecting an AC current flowing between the electrodes 1 in a state where the voltage is applied from the AC power supply to the electrodes 1. A detailed explanation thereof is omitted because it is described, for example, in Patent Literature 1.

The temperature measurement circuit 11 is connected to the temperature sensor 3 and can measure a temperature of the insulating gas in the vicinity of the solid electrolyte membrane 2 (temperature measurement unit). The temperature measurement circuit 11 includes, for example, a direct-current (DC) power supply (not shown) that applies a voltage to the temperature sensor 3; and a voltage divider-resistor (not shown) that detects a current flowing in the temperature sensor 3.

The computation unit 12 includes a computing function and a control processing function. The computation unit 12 particularly functions as a water-concentration detection unit, and can calculate a water concentration based on an impedance value obtained from the impedance measurement circuit 10 and a measured temperature obtained from the temperature measurement circuit 11. Furthermore, the computation unit 12 can control opening and closing of the valve 6. The display unit 13 can display an output of the computation unit 12. While the water-concentration detection device 30 also includes other constituent elements such as an input unit that executes a control over the water-concentration detection device 30, such elements are omitted from FIG. 1.

Figure 2:
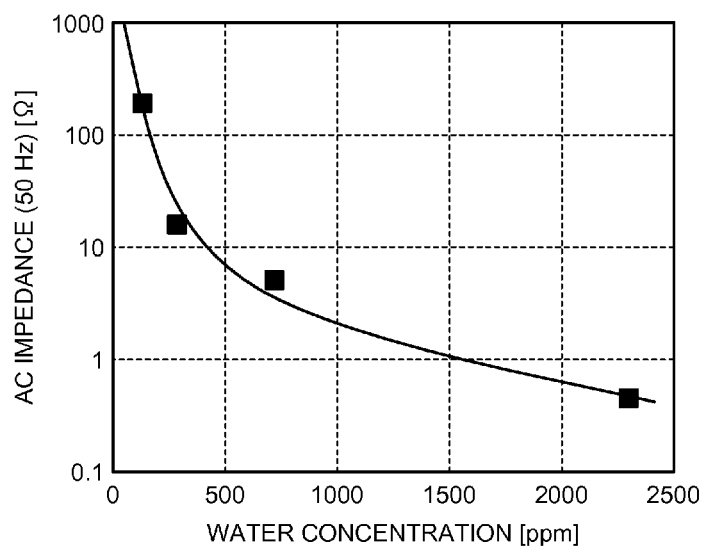
FIG. 2 is a graph of an example of a relation between a water concentration of insulating gas and an AC impedance of a solid electrolyte membrane.

A water-concentration detection process performed by the computation unit 12 is specifically explained here. Under a condition of a constant temperature of the insulating gas, a relation shown in, for example, FIG. 2 is present between the water concentration of the insulating gas and the AC impedance of the solid electrolyte membrane 2. FIG. 2 is a graph indicating a relation between a water concentration (ppm) of insulating gas and an AC impedance ($\Omega$) of the solid electrolyte membrane 2 in a case where the temperature is a certain value, and the graph is created based on measurement results. As an example, FIG. 2 depicts results acquired at a power supply frequency of 50 hertz. As shown in FIG. 2, the AC impedance monotonically decreases to correspond to the increase in the water concentration. Therefore, if data indicating the relation shown in FIG. 2, specifically the data for allocating the water concentration to correspond to the AC impedance, is given to the computation unit 12 in advance (or stored in a storage device (not shown) connected to the computation unit 12), the computation unit 12 can obtain the water concentration corresponding to the value of an impedance obtained from the impedance measurement circuit 10 by referring to the data given in advance at least in an environment in which the temperature is the certain value.

Figure 3:
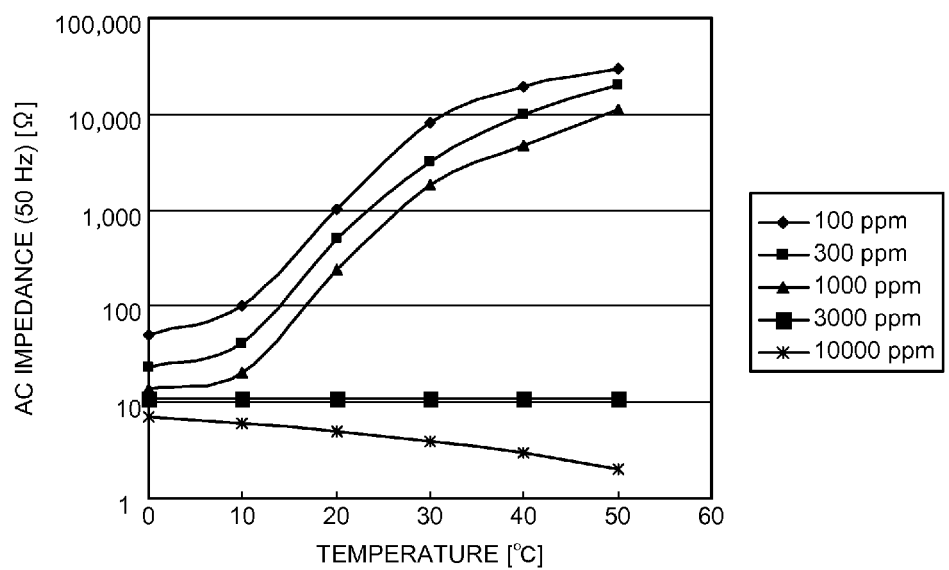
FIG. 3 is a graph of a relation between a temperature and an impedance with respect to a plurality of different water concentrations.

Generally, an internal temperature of the gas-insulated device 20 changes by as high as several tens of degrees centigrade when the gas-insulated device 20 is installed outdoors. Therefore, at a time of detecting the water concentration, it is normally necessary to consider temperature dependencies of the AC impedance. In a first embodiment, the temperature sensor 3 arranged in the vicinity of the solid electrolyte membrane 2 is used to measure the temperature of the insulating gas, and matrix data for allocating the water concentration to correspond to the temperature and the AC impedance is given to the computation unit 12 in advance (or stored in a storage device (not shown) connected to the computation unit 12 in advance). With this configuration, the computation unit 12 can output the water concentration corresponding to the value of an impedance obtained from the impedance measurement circuit 10 and the measured temperature obtained from the temperature measurement circuit 11 as a detected value by referring to this matrix data. For example, the matrix data can be created as follows. FIG. 3 is a graph indicating a relation between a temperature and an impedance with respect to a plurality of different water concentrations. In FIG. 3, five different curves represent cases where the water concentrations are 100 (ppm), 300 (ppm), 1000 (ppm), 3000 (ppm), and 10000 (ppm), respectively. The matrix data for allocating each of the water concentrations to correspond to the impedance and the temperature can be obtained by discretizing each of the impedance and the temperature. As shown in FIG. 3, at the water concentration lower than 3000 (ppm), the impedance increases as the temperature rises. At the water concentration higher than 3000 (ppm), the impedance decreases as the temperature rises.

The water-concentration detection process using the impedance element 7 is explained next. When the insulating gas is introduced into the gas chamber 31a, a water amount of the solid electrolyte membrane 2 is in a state of equilibrium with the water contained in the insulating gas in due time. Thereafter, when the AC voltage is applied to the electrodes 1, the impedance measurement circuit 10 measures the AC impedance corresponding to the water concentration of the solid electrolyte membrane 2. The impedance measurement circuit 10 outputs a measured impedance value to the computation unit 12. The temperature measurement circuit 11 outputs the measured temperature of the insulating gas detected by the temperature sensor 3 to the computation unit 12. The computation unit 12 obtains the water concentration corresponding to the measured impedance value and the measured temperature while referring to the matrix data given to the computation unit 12 in advance. The computation unit 12 transmits the obtained water concentration to the display unit 13 and the display unit 13 displays the water concentration.

Meanwhile, the gas chamber 31 of the water-concentration detection device 30 is in a state of being filled with the ordinary air in an atmospheric environment or with the sampling gas used in a previous measurement before starting measuring the water concentration. The water concentration of the air is possibly several tens of thousands of ppm (10000 ppm) or more. The water concentration of the insulating gas in the actually used gas-insulated device 20 is normally several tens of ppm to several hundreds of ppm. Therefore, a large concentration difference is present between the water concentration of the insulating gas and that of the air. An influence of the concentration difference on the measurement will be explained below.

Figure 4:
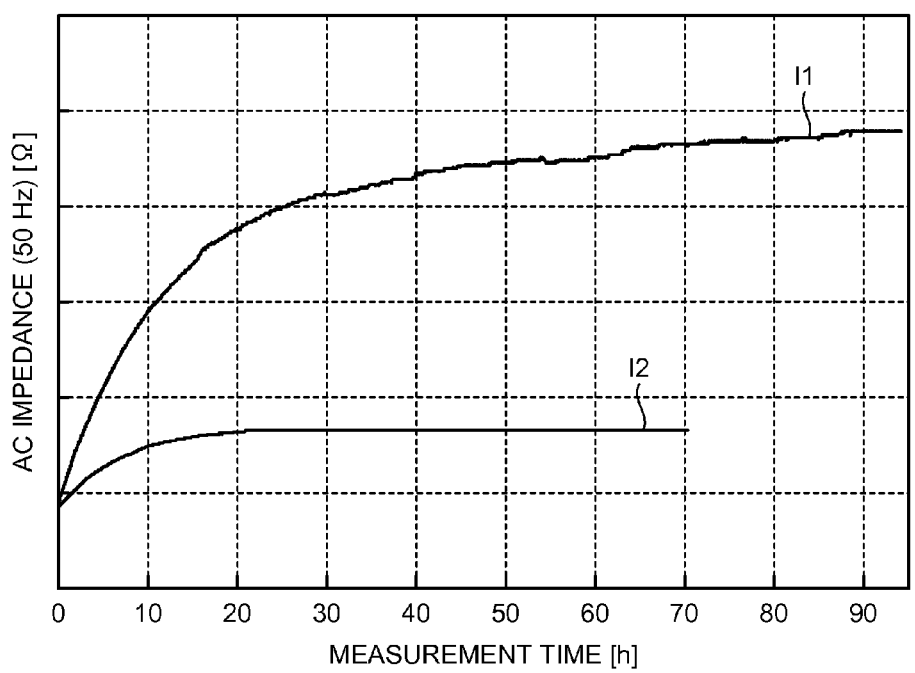
FIG. 4 is an example of time change curves of an AC impedance measured by an impedance element 7.

FIG. 4 is an example of time change curves of an AC impedance measured by the impedance element 7. FIG. 4 is obtained by placing the impedance element 7, previously placed in the atmospheric atmosphere, in an environment of a predetermined water concentration and measuring the time change in the AC impedance. In FIG. 4, a curve I1 denotes a measurement result in a case where the water concentration is several tens of ppm, and a curve I2 denotes a measurement result in a case where the water concentration is several hundreds of ppm. As can be confirmed from FIG. 4, the curve I2 in the case where the water concentration of the insulating gas is the higher (closer to the atmospheric atmosphere) tends to converge faster and the curve I1 in the case where the water concentration is the lower (further from the atmospheric atmosphere) tends to take a longer time to converge.

In this way, when the water content of the solid electrolyte membrane 2 is close to the water concentration of the insulating gas that is a measurement target at a time of starting the measurement, a response of the impedance element 7 converges in a short period of time, while when the water content greatly differs from the water concentration of the insulating gas, then the response of the impedance element 7 does not converge in a short period of time and it is difficult to promptly obtain a final measured value.

That is, to obtain the final "measured value" in a short period of time, it is preferable to place the impedance element 7 in a state as close as possible to a water state of the insulating gas that is the measurement target from the beginning of the measurement. It is thereby possible to obtain the measurement result of the water concentration of the insulating gas in a short period of time.

Therefore, in the first embodiment, the absorptive absorbent 42 is placed in the gas chamber 31b, and the valve 6 is opened, for example, at times other than the time of measuring the water concentration to make the gas chambers 31a and 31b into a state of communicating with each other via the communication path 5; or the valve 6 is opened, for example, within a predetermined time before the start of measuring the water concentration to make the gas chambers 31a and 31b into the state of communicating with each other via the communication path 5. This makes an interior of the gas chamber 31a into an extremely dry state before the start of measuring the water concentration. With this configuration, the solid electrolyte membrane 2 is in a state of equilibrium with this dry atmosphere and the water contained in the solid electrolyte membrane 2 decreases considerably. At the start of measuring the water concentration, the valve 6 is closed first to make the gas chamber 31a into a state of being isolated from the gas chamber 31b so as to prevent the absorbent 42 from influencing the measurement of the water concentration, and the valve 22 of the pipe 21 is then opened to introduce the insulating gas within the gas-insulated device 20 into the gas chamber 31a. The valve 6 is closed during the measurement.

The water content of the solid electrolyte membrane 2 arranged in the insulating gas within the gas chamber 31a reaches a state of equilibrium with the water concentration of the insulating gas in a short period of time because the water content of the solid electrolyte membrane 2 is already reduced. That is, in the first embodiment, because the water content of the solid electrolyte membrane 2 at the time of starting the measurement is reduced so as to be close to the water concentration of the insulating gas by using the absorbent 42, the value of impedance converges in a short period of time after starting the measurement. The subsequent water-concentration detection process performed by the impedance measurement circuit 10, the temperature measurement circuit 11, and the computation unit 12 is as described above. While an amount of the absorbent 42 has an effect on a dehumidification capability, the amount can be determined according to the approximate water concentration (normally several tens of ppm to several hundreds of ppm) of the insulating gas that is the measurement target.

The opening and closing of the communication path 5 by the valve 6 is controlled by the computation unit 12. For example, an open/close signal for the valve 6 can be input to the computation unit 12 by operating the input unit of the water-concentration detection device 30, and the computation unit 12 may be configured to control the valve 6 to open or close in response to a content of the open/close signal when the computation unit 12 receives the open/close signal. Alternatively, the computation unit 12 may be configured to automatically recognize the start or end of the measurement of the water concentration and to control the valve 6 to turn into an open state when the measurement ends; or to control the valve 6 to turn into a closed state when the measurement starts.

In this way, in the first embodiment, the atmosphere within the gas chamber 31a where the entire impedance element 7 is arranged is made into an extremely dry state close to a state of the water concentration of the insulating gas within the gas-insulated device 20 in advance by using the absorbent 42 as a drying unit. This shortens the time required until the water content of the solid electrolyte membrane 2 reaches the state of equilibrium with the water concentration of the insulating gas. Therefore, there is an effect that it is possible to perform the measurement of the water concentration in a short period of time.

Generally, the water sensor is not intended to be used at a region of an extremely low water concentration as described in the first embodiment because the water sensor is used for purposes of a humidity control or the like. However, in a case of measuring the water concentration of the insulating gas within the gas-insulated device 20, the water sensor measures the water concentration in excess of a general measurement range and the problem of the measurement time conspicuously occurs. In a case of measuring atmospheric humidity, a measurement result is normally output in a few minutes after the start of the measurement. However, in a case of the presence of the extraordinary water concentration difference between the water concentration of the measurement target and an initial water content of the solid electrolyte membrane 2, particularly in a case where the water concentration of the measurement target is much lower, it is necessary to sufficiently dehumidify the solid electrolyte membrane 2 and it takes quite a long time before the solid electrolyte membrane 2 reaches the state of being sufficiently dehumidified. Therefore, it can be said that the first embodiment provides quite effective means for shortening the measurement time for measuring the water concentration of the insulating gas within the gas-insulated device 20.

In the first embodiment, the water concentration is detected by measuring the AC impedance of the solid electrolyte membrane 2 and the gas temperature near the solid electrolyte membrane 2. At that time, the water concentration is detected using the matrix data obtained in advance based on the measurement results of the AC impedance and the measurements of the temperature. Therefore, according to the first embodiment, it is possible to reduce a measurement error in the water concentration because the water concentration can be accurately measured without being subjected to the influence of the temperature.

In the first embodiment, the matrix data (table data) in which a water concentration is allocated to the impedance and the temperature is prepared in advance so as to obtain the water concentration in view of the temperature characteristics of the solid electrolyte membrane 2, and the water concentration is obtained by referring to this matrix data. However, a method for obtaining a water concentration is not limited by use of the matrix, and any means may be used as long as a water concentration is allocated to correspond to the impedance and the temperature, and the allocation may be made by, for example, a function.

In an environment in which the temperature of the insulating gas is substantially constant, the temperature dependency of the impedance can be ignored. Therefore, in this case, it is not always necessary to provide the temperature sensor 3 and the temperature measurement circuit 11, and it suffices to prepare the data (table data) for allocating the water concentration to correspond to the impedance in advance and the computation unit 12 can obtain the water concentration by referring to this data.

Second Embodiment

Figure 5:
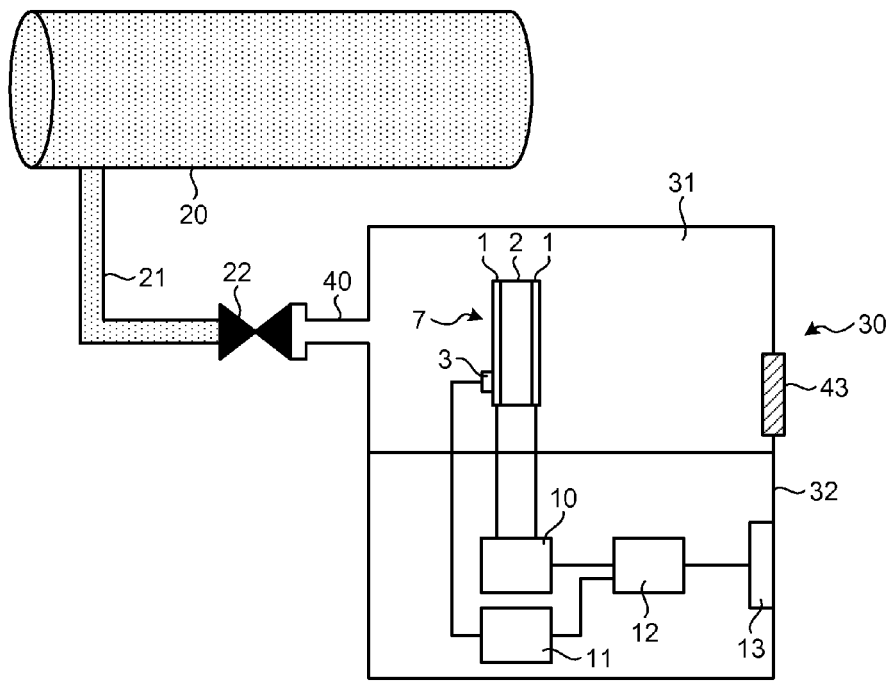
FIG. 5 is a configuration diagram of a water-concentration detection device according to a second embodiment.

FIG. 5 is a configuration diagram of a water-concentration detection device according to a second embodiment of the present invention. In FIG. 5, constituent elements identical to those shown in FIG. 1 are denoted by like reference signs. In the first embodiment, the absorbent 42 is installed in the gas chamber 31b so as to make the gas chamber 31a where the impedance element 7 is installed into the environment close to the water state in the gas-insulated device 20. In the second embodiment, the water-concentration detection device 30 is configured such that the water in the gas chamber 31 is discharged to outside of the gas chamber 31 and such that a dehumidifier making an environment in the gas chamber 31 into an extremely dry state is provided in the gas chamber 31 before the start of the measurement, as shown in FIG. 5.

That is, in the second embodiment, the gas chamber 31 is used as a single chamber without providing the wall 4, the communication path 5, the valve 6, and the absorbent 42 used in the first embodiment, and a dehumidifier 43 serving as the drying unit is installed in the gas chamber 31. The dehumidifier 43 can make the atmosphere in the gas chamber 31 into the extremely dry state by removing the water in the atmosphere in the gas chamber 31 and discharging the water to outside of the water-concentration detection device 30. An ON/OFF switch (not shown) is provided on the dehumidifier 43 and the dehumidifier 43 can be started or stopped by operating the ON/OFF switch.

In the second embodiment, the interior of the gas chamber 31 is made into an extremely dry state before the start of measuring the water concentration by starting the dehumidifier 43, for example, within a predetermined time before the start of measuring the water concentration. An operating time of the dehumidifier 43 is set according to the approximate water concentration (normally several tens of ppm to several hundreds of ppm) of the insulating gas that is the measurement target. At the time of starting measuring the water concentration, the dehumidifier 43 is stopped to prevent the presence of the dehumidifier 43 from influencing the measurement of the water concentration, the valve 22 of the pipe 21 is then opened, and the insulating gas within the gas-insulated device 20 is introduced into the gas chamber 31.

The water content of the solid electrolyte membrane 2 arranged in the insulating gas within the gas chamber 31 reaches a state of equilibrium with the water concentration of the insulating gas in a short period of time because the water content of the solid electrolyte membrane 2 is already reduced. That is, in the second embodiment, because the water content of the solid electrolyte membrane 2 at the time of starting the measurement is reduced so as to be close to the water concentration of the insulating gas by using the dehumidifier 43, the measured value of the impedance converges in a short period of time after starting the measurement. The subsequent water-concentration detection process is as described in the first embodiment.

According to the second embodiment, the dehumidifier 43 is installed in the gas chamber 31 and the atmosphere in the gas chamber 31 is made into an extremely dry state before the start of the measurement. This shortens the time required before the water content of the solid electrolyte membrane 2 reaches the state of equilibrium with the water concentration of the insulating gas. Therefore, there is an effect that it is possible to perform the measurement of the water concentration in a short period of time. Other configurations, operations, and effects of the second embodiment are identical to those of the first embodiment.

Third Embodiment

Figure 6:
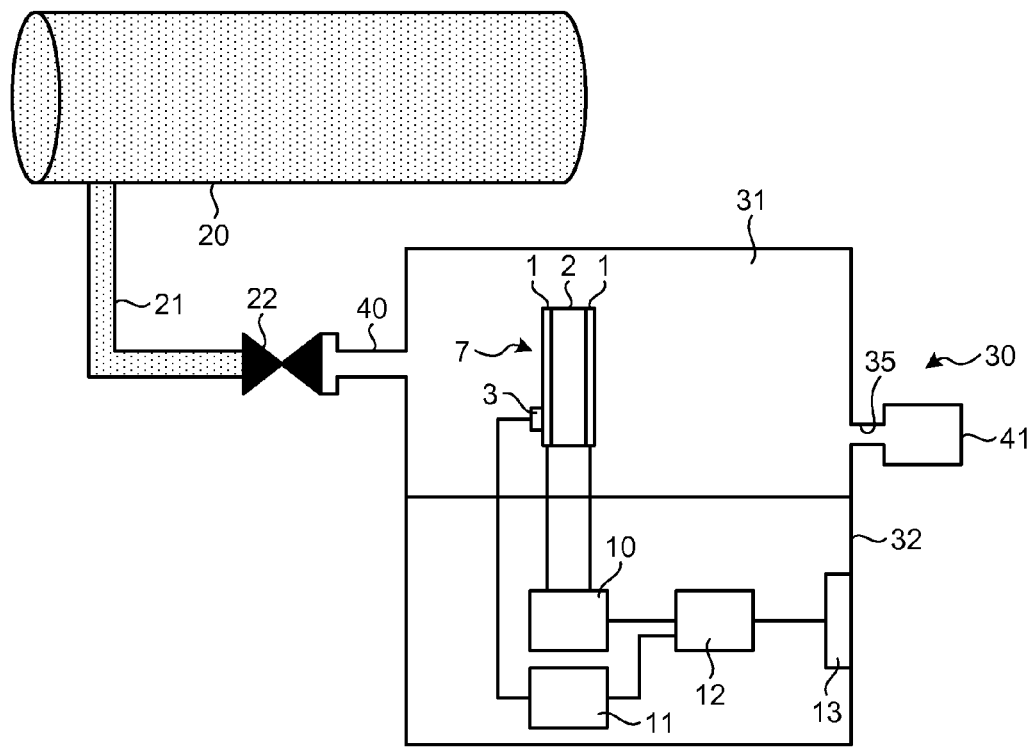
FIG. 6 is a configuration diagram of a water-concentration detection device according to a third embodiment.

FIG. 6 is a configuration diagram of a water-concentration detection device according to a third embodiment of the present invention. In FIG. 6, constituent elements identical to those shown in FIG. 5 are denoted by like reference signs. In the second embodiment, the dehumidifier 43 is installed in the gas chamber 31 so as to make the gas chamber 31 where the impedance element 7 is installed into the environment close to the water state in the gas-insulated device 20 before the start of the measurement. In the third embodiment, the water-concentration detection device 30 is configured so that a vacuum pump 41 is provided outside of the water-concentration detection device 30, this vacuum pump 41 is connected to an exhaust port 35 of the gas chamber 31, and so that the vacuum pump 41 is started to discharge the gas within the gas chamber 31 together with the water contained in the gas to outside of the gas chamber 31 and the interior of the gas chamber 31 is made into an extremely dry state before the start of the measurement, as shown in FIG. 6.

That is, in the third embodiment, the exhaust port 35 connected to the gas chamber 31 is provided and the vacuum pump 41 serving as the drying unit is connected to the exhaust port 35 in place of providing the dehumidifier 43 according to the second embodiment. A valve (not shown) is provided on the exhaust port 35 and the gas chamber 31 can be hermetically sealed by closing this valve when the vacuum pump 41 is detached.

In the third embodiment, the interior of the gas chamber 31 is made into an extremely dry state at least just before the start of measuring the water concentration by starting the vacuum pump 41, for example, within a predetermined time before the start of measuring the water concentration. An operating time of the vacuum pump 41 is set according to the approximate water concentration (normally several tens of ppm to several hundreds of ppm) of the insulating gas that is the measurement target. At the time of starting the measurement of the water concentration, the vacuum pump 41 is stopped to prevent the presence of the vacuum pump 41 from influencing the measurement of the water concentration, the valve 22 of the pipe 21 is then opened, and the insulating gas within the gas-insulated device 20 is introduced into the gas chamber 31.

The water content of the solid electrolyte membrane 2 arranged in the insulating gas within the gas chamber 31 reaches a state of equilibrium with the water concentration of the insulating gas in a short period of time because the water content of the solid electrolyte membrane 2 is already reduced. That is, in the third embodiment, because the water content of the solid electrolyte membrane 2 at the time of starting the measurement is reduced so as to be close to the water concentration of the insulating gas by using the vacuum pump 41, the measured value of the impedance converges in a short period of time after starting the measurement. The subsequent water-concentration detection process is as described in the first and second embodiments.

Similarly to the second embodiment, the third embodiment also has an effect that it is possible to perform the measurement of the water concentration in a short period of time. Other configurations, operations, and effects of the third embodiment are identical to those of the second embodiment.

Fourth Embodiment

Figure 7:
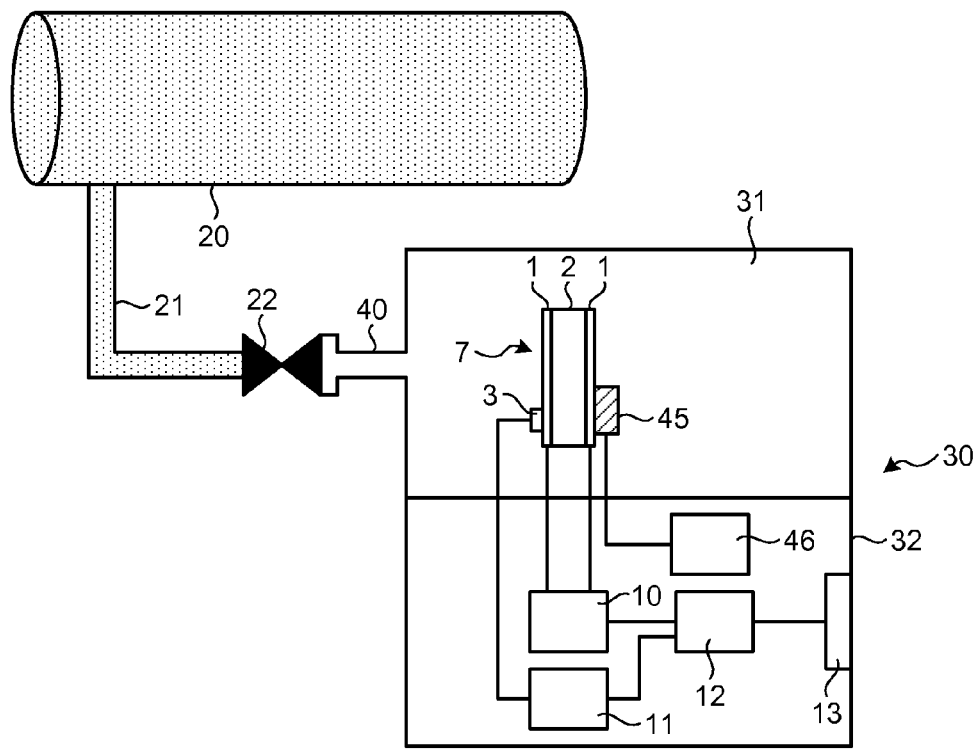
FIG. 7 is a configuration diagram of a water-concentration detection device according to a fourth embodiment.

FIG. 7 is a configuration diagram of a water-concentration detection device according to a fourth embodiment. In FIG. 7, constituent elements identical to those shown in FIG. 1 are denoted by like reference signs. In the first embodiment, the absorbent 42 is installed in the gas chamber 31b so as to make the gas chamber 31a where the impedance element 7 is installed into the environment close to the water state in the gas-insulated device 20. In the fourth embodiment, the water-concentration detection device 30 is configured so that a heater 45 is installed, for example, on a surface of one of the electrodes 1 and the surface of the electrode 1 is heated by this heater 45, thereby accelerating removal of the water contained in the solid electrolyte membrane 2, as shown in FIG. 7.

That is, in the fourth embodiment, the gas chamber 31 is used as the single chamber without providing the wall 4, the communication path 5, the valve 6, and the absorbent 42 used in the first embodiment, and the heater 45 is installed on the surface of the electrode 1 in the gas chamber 31. Furthermore, a heater control unit 46 that controls heating by the heater 45 is provided in the signal processing unit 32. The heater control unit 46 may be configured, for example, so as to be further controlled by the computation unit 12. While the heater 45 can be provided at least on the surface of one of the electrodes 1, it is preferable to provide the heater 45 on the electrode 1 facing the electrode 1 on which the temperature sensor 3 is installed (see FIG. 7). This configuration is for preventing local heating by the heater 45 from influencing the temperature measurement performed by the temperature sensor 3.

In the fourth embodiment, the water is removed from the solid electrolyte membrane 2 by heating the impedance element 7 with the heater 45 before starting the measurement. Although the longer the heating time, the more preferable it is, the heating should continue at least for a predetermined time. At the start of measuring the water concentration, the heater 45 is stopped, the valve 22 of the pipe 21 is then opened, and the insulating gas within the gas-insulated device 20 is introduced into the gas chamber 31. The heater 45 is stopped during the measurement.

The water content of the solid electrolyte membrane 2 reaches a state of equilibrium with the water concentration of the insulating gas in a short period of time because the water content of the solid electrolyte membrane 2 is reduced in advance by controlling the heater 45 to heat the impedance element 7 with respect to insulating gas as a measurement target that is introduced from the gas-insulated device 20 into the gas chamber 31 and that is the measurement target. The subsequent water-concentration detection process is as described in the first to third embodiments.

According to the fourth embodiment, there is an effect that it is possible to perform the measurement of the water concentration in a short period of time by reducing the water content of the solid electrolyte membrane 2 in advance by heating the impedance element 7 with the heater 45. Other configurations, operations, and effects of the fourth embodiment are identical to those of the first to third embodiments.

Fifth Embodiment

Figure 8:
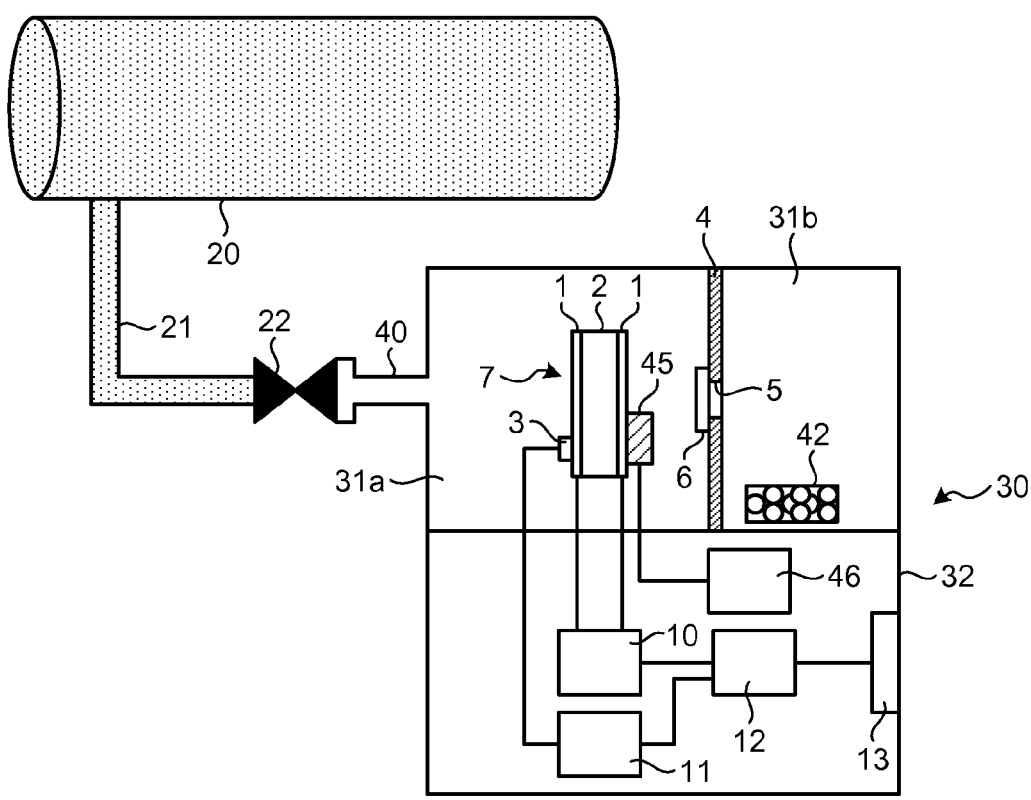
FIG. 8 is a configuration diagram of a water-concentration detection device according to a fifth embodiment.

FIG. 8 is a configuration diagram of a water-concentration detection device according to a fifth embodiment of the present invention. In FIG. 8, constituent elements identical to those shown in FIG. 1 and FIG. 7 are denoted by like reference signs. The fifth embodiment is an embodiment in which the fourth embodiment is applied to the first embodiment. As shown in FIG. 8, the heater 45 and the heater control unit 46 are further provided in addition to the configuration of the first embodiment.

In the fifth embodiment, before the start of the measurement, the adsorbent 42 is used to make the interior of the gas chamber 31a into an extremely dry state as described in the first embodiment and the heater 45 is used to accelerate withdrawing the water from within the solid electrolyte membrane 2 as described in the fourth embodiment. Accordingly, there is an effect that it is possible to further shorten the measurement time of the water concentration. Other configurations, operations, and effects of the fifth embodiment are identical to those of the first to third embodiments.

Although not shown in the drawings, similarly to the fifth embodiment, it is also possible to form a configuration in which the fourth embodiment is applied to the second embodiment and a configuration in which the fourth embodiment is applied to the third embodiment, and these combinations can achieve effects that are identical to those of the fifth embodiment.

INDUSTRIAL APPLICABILITY

As described above, the present invention is suitable for detecting a water concentration of insulating gas filled in a gas-insulated device.

REFERENCE SIGNS LIST 1 electrode
2 solid electrolyte membrane
3 temperature sensor
4 wall
5 communication path
6 valve
7 impedance element
10 impedance measurement circuit
11 temperature measurement circuit
12 computation unit
13 display unit
20 gas-insulated device
21 pipe
22 valve
30 water-concentration detection device
31, 31a, 31b gas chamber
32 signal processing unit
35 exhaust port
40 attachment port
41 vacuum pump
42 absorbent
43 dehumidifier
45 heater
46 heater control unit

The invention claimed is:

1. A water-concentration detection device configured to detect a water concentration of insulating gas filled in a gas-insulated device, the water-concentration detection device comprising:
   a gas chamber that introduces the insulating gas from the gas-insulated device via a pipe provided with a first valve that controls the amount of insulating gas that enters the gas chamber, and the gas chamber encloses therein the insulating gas;
   electrodes that are porous and are arranged to face each other within the gas chamber;
   a solid electrolyte membrane that is hydrogen-ion conductive and is held between and fixedly attached to the electrodes;
   an impedance measurement unit that measures an alternating-current impedance between the electrodes by applying an alternating-current voltage to the electrodes;
   a water-concentration detection unit that detects the water concentration of the insulating gas based on the alternating-current impedance measured by the impedance measurement unit; and
   a drying unit arranged on a downstream side of the solid electrolyte membrane with respect to a direction in which the insulating gas is introduced into the gas chamber, wherein
   (1) the drying unit removes water from an atmosphere in the gas chamber in a state in which the first valve is closed so that no insulating gas enters the gas chamber;
   (2) the insulating gas is subsequently introduced into the gas chamber from the gas-insulated device in a state in which the first valve is opened; and
   (3) the water-concentration detection unit detects the water concentration of the insulating gas after the first valve is opened and the insulating gas is introduced into the gas chamber.

2. The water-concentration detection device according to claim 1, wherein
   the gas chamber includes a first gas chamber in which the electrodes and the solid electrolyte membrane are arranged and a second gas chamber, the gas chamber being partitioned into the first gas chamber and the second gas chamber by a wall, wherein
   a communication path that communicates the first gas chamber with the second gas chamber and a second valve that opens or closes the communication path are provided on the wall,
   the second valve is in an open state at least within a predetermined time before start of measuring the water concentration, and is in a closed state during a measurement of the water concentration, and
   the drying unit is an absorptive absorbent installed in the second gas chamber.

3. The water-concentration detection device according to claim 1, wherein the drying unit is a dehumidifier installed in the second gas chamber and removes water from the gas chamber.

4. The water-concentration detection device according to claim 1, wherein the drying unit is a vacuum pump installed outside of the gas chamber and connected to the gas chamber via an exhaust port.

5. The water-concentration detection device according to claim 1, further comprising a heater unit that is provided at least on a surface of one of the electrodes and that accelerates removal of water contained in the solid electrolyte membrane, wherein
   the heater unit is in a heating state at least within a predetermined time before start of measuring the water concentration, and is in a heating stopped state during the measurement of the water concentration.

6. The water-concentration detection device according to claim 1, comprising a temperature measurement unit that measures a temperature of the insulating gas using a temperature sensor arranged near the solid electrolyte membrane, wherein
   the water-concentration detection unit detects the water concentration of the insulating gas based on the alternating-current impedance measured by the impedance measurement unit and the temperature measured by the temperature measurement unit.

7. The water-concentration detection device according to claim 6, wherein the water-concentration detection unit holds matrix data for allocating a water concentration to correspond to a temperature and an alternating-current impedance in advance, and outputs the water concentration corresponding to the alternating-current impedance measured by the impedance measurement unit and the temperature measured by the temperature measurement unit as a detected value while referring to the matrix data.

* * * * *